United States Patent [19]
Hissong et al.

[11] Patent Number: 5,669,501
[45] Date of Patent: Sep. 23, 1997

[54] PACKAGE AND METHOD FOR DELIVERING A MEDICAL IMPLANT

[75] Inventors: James B. Hissong, Jacksonville, Fla.; John E. Studer, Morris Plains, N.J.

[73] Assignee: Xomed Surgical Products, Inc., Jacksonville, Fla.

[21] Appl. No.: 658,283

[22] Filed: Jun. 5, 1996

[51] Int. Cl.$^6$ ............................................. A61B 19/00
[52] U.S. Cl. ........................ 206/438; 206/363; 206/565; 206/588
[58] Field of Search ........................ 206/438, 363, 206/364, 365, 814, 588, 564, 565, 467, 468, 488

[56] References Cited

U.S. PATENT DOCUMENTS

| 3,380,489 | 4/1968 | Harautuneian | 206/364 |
| 5,193,679 | 3/1993 | White | 206/438 |
| 5,323,900 | 6/1994 | Atkins et al. | 206/365 |
| 5,379,895 | 1/1995 | Foslien | 206/814 |
| 5,386,908 | 2/1995 | Sinn | 206/363 |
| 5,485,917 | 1/1996 | Early | 206/363 |
| 5,568,865 | 10/1996 | Mase et al. | 206/363 |

*Primary Examiner*—Paul T. Sewell
*Assistant Examiner*—Luan K. Bui

[57] ABSTRACT

A package for sterile delivery of medical implants such as, for example, wire piston prostheses, includes a tray defining a compartment, an insert removably disposed in the tray, and a lid mounted by the tray for sliding movement relative thereto. The medical implant is held by the insert in a specific position above a bottom wall of the compartment and with a longitudinal axis of the implant aligned with a recess in a wall of the compartment to permit the implant to be grasped with forceps for proper presentation at the operative site.

16 Claims, 3 Drawing Sheets

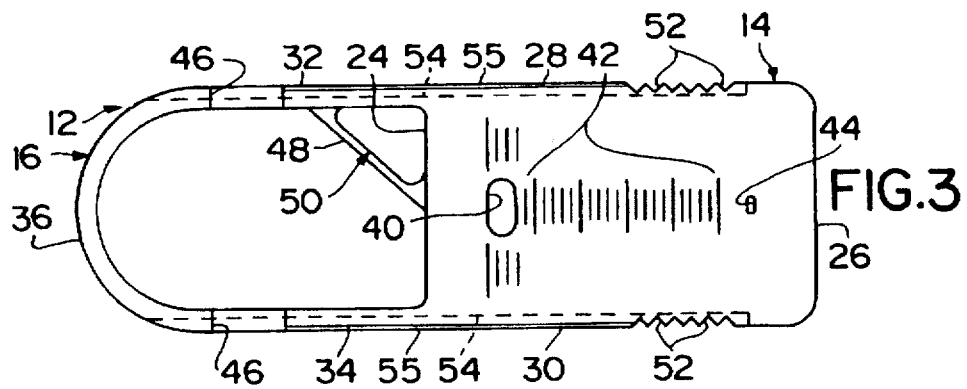
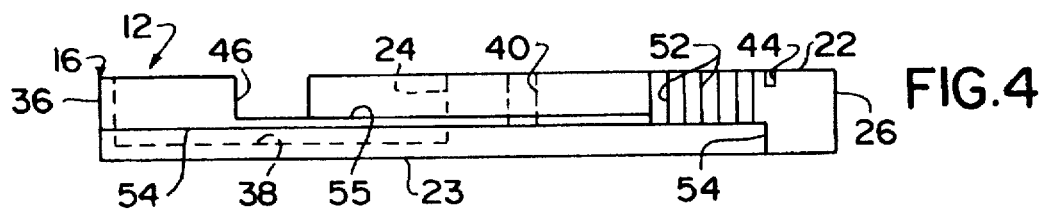
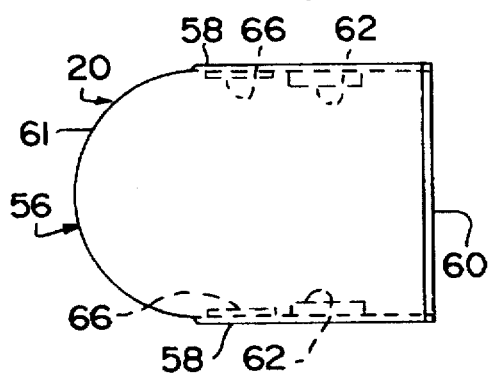
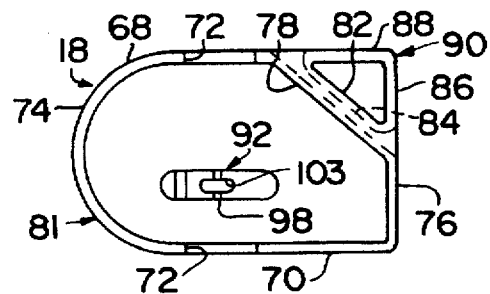
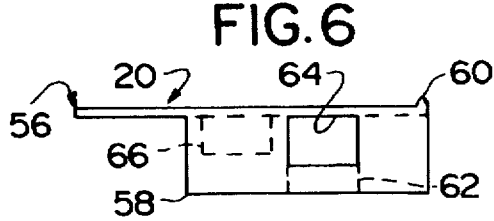
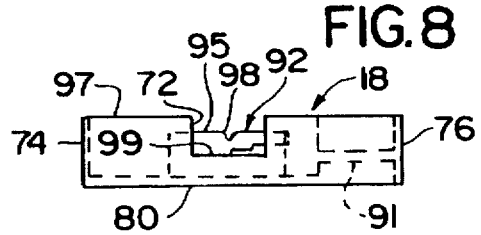
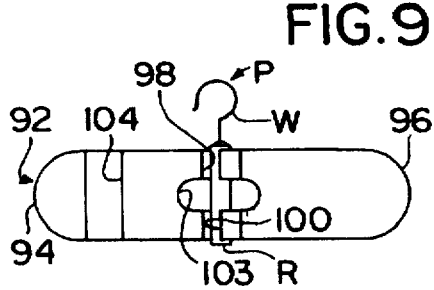
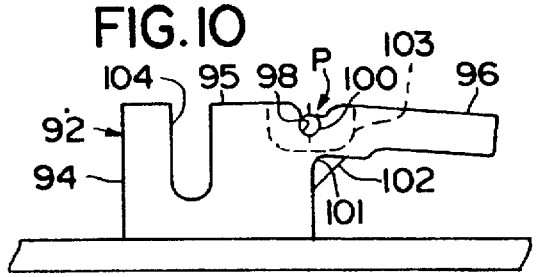

PACKAGE AND METHOD FOR DELIVERING A MEDICAL IMPLANT

FILED OF THE INVENTION

The present invention relates generally to packaging and methods for sterile delivery of small medical implants and, more particularly, to a package and method for sterile delivery of a middle ear prosthesis such as, for example, a wire piston prosthesis.

DISCUSSION OF THE RELATED ART

Small medical implants, such as wire piston prostheses inserted between the incus and the oval window in the middle ear as part of a stapedectomy, are typically delivered to medical personnel in molded packages having one or more cavities or compartments and a lid for closing the compartments. The wire piston prostheses each include a piston rod with a wire loop at a proximal end and are not restrained within the compartments but, rather, are free to move about when the package is opened. Forceps are normally used to grasp a wire piston prosthesis out of one of the compartments for use during the operative procedure; however, this is a difficult and time consuming maneuver because the prosthesis is small and free to move about or float within the compartment. Additionally, once the prosthesis is removed from the package, the prosthesis must be regrasped such that the forceps jaws engage the wire loop to allow insertion of the distal end of the piston rod directly into a stapedotomy opening formed in the stapes footplate or onto a graft covering the oval window in the case of the stapes footplate having been removed.

SUMMARY OF THE INVENTION

Accordingly, it is a primary object of the present invention to overcome the disadvantages of the prior art and to facilitate removal of small medical implants from a sterile delivery package.

Another object of the present invention is to prevent movement of a small medical implant in a compartment of a sterile delivery package.

It is a further object of the present invention to mount a small medical implant in a specified position or orientation above the bottom wall of a compartment of a sterile delivery package to facilitate grasping of the medical implant with forceps.

The present invention has an additional object in mounting a small medical implant above the bottom wall of a compartment of a sterile delivery package with a longitudinal axis of the medical implant disposed to permit grasping of the medical implant with a forceps having a longitudinal axis coaxially aligned with the longitudinal axis of the medical implant.

Some advantages of the present invention over the prior art are that the package of the present invention prevents movement of small medical implants, such as wire piston prostheses, during transport, sterilization and delivery of the prostheses, that quick removal of small medical implants from the package is more adequately assured, and that the package is configured to hold a medical implant in a specified position or orientation to facilitate grasping of a proximal end of the medical implant with the jaws of a forceps so that the forceps can be used to introduce the distal end of the medical implant at the operative site without the need of having to reposition the medical implant within the jaws of the forceps.

The present invention is generally characterized in a medical implant and a package for sterile delivery of the medical implant including a tray defining a compartment having a bottom wall and at least one wall extending upwardly from the bottom wall, a lid configured to cover the compartment, and means for holding the medical implant in a specified position above the bottom wall of the compartment during transport and removal. At least a portion of the upwardly extending wall of the compartment is lower than the medical implant in the specified position, and a longitudinal axis of the medical implant in the specified position is aligned with the lower portion of the upwardly extending wall to permit the medical implant to be grasped with a forceps positioned along the lower portion of the wall and having a longitudinal axis substantially aligned with the longitudinal axis of the medical implant. In a preferred embodiment, the medical implant is held in the specified position within a slot formed in a pedestal extending upwardly from the bottom wall of the compartment. The pedestal can be mounted directly within the compartment or can be carried by an insert removably disposed within the compartment. If the pedestal is carried by an insert, the insert is preferably formed of a soft material to reduce the chance for breakage of the implant during shipping and to allow instruments to "dig into" the material to get under the medical implant for better presentation. Preferably, the tray will also include a handle disposed proximally of the compartment; and, when the medical implant is a wire piston prosthesis, the handle will preferably have a planar surface with scale markings and/or recesses for use in measuring and trimming the prosthesis.

Another aspect of the present invention is generally characterized in a medical implant and a package for sterile delivery of the medical implant including a tray defining a compartment having a bottom wall, a lid configured to cover the compartment, and a pedestal extending upwardly from the bottom wall of the compartment when the tray is oriented horizontally. The pedestal includes a slot configured to hold the medical implant in a specified position above the bottom wall of the compartment and a lever arm extending in cantilevered relation to the slot. The lever arm is movable between an elevated position holding the medical implant in the slot and a depressed position releasing the medical implant from the slot.

Yet another aspect of the present invention is generally characterized in a method for sterile delivery of a medical implant including the steps of holding the medical implant in a specified position within a compartment of a sterile delivery package so that the medical implant is spaced from a bottom wall of the compartment and a longitudinal axis of the implant is aligned with a recess in a wall of the compartment, positioning a forceps in the recess such that a longitudinal axis of the forceps is substantially aligned with the longitudinal axis of the medical implant, grasping the medical implant with the forceps, removing the medical implant from the compartment, and inserting the medical implant into the body in the condition in which it was grasped. In a preferred embodiment, the holding step includes mounting the medical implant in a slot formed in a pedestal extending upwardly from the bottom wall of the compartment and the removing step includes depressing a lever extending in cantilevered relation to the slot to release the medical implant therefrom.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 is a top plan view of the tray of the package.

FIG. 4 is a side elevational view of the tray of the package.

FIG. 5 is a top plan view of the lid of the package.

FIG. 6 is a side elevational view of the lid of the package.

FIG. 7 is a top plan view of the insert of the package.

FIG. 8 is a side elevational view of the insert of the package.

FIG. 9 is an enlarged fragmentary top view of the pedestal in the insert holding a wire piston prosthesis.

FIG. 10 is an enlarged fragmentary side view of the pedestal.

DETAILED DESCRIPTION OF THE PREFERRED EMBODIMENT

The package of the present invention is described hereinafter for use in delivering a wire piston prosthesis in sterile condition. It is understood, however, that the package of the present invention can be used for sterile delivery of any type of medical implant.

Figure 1:
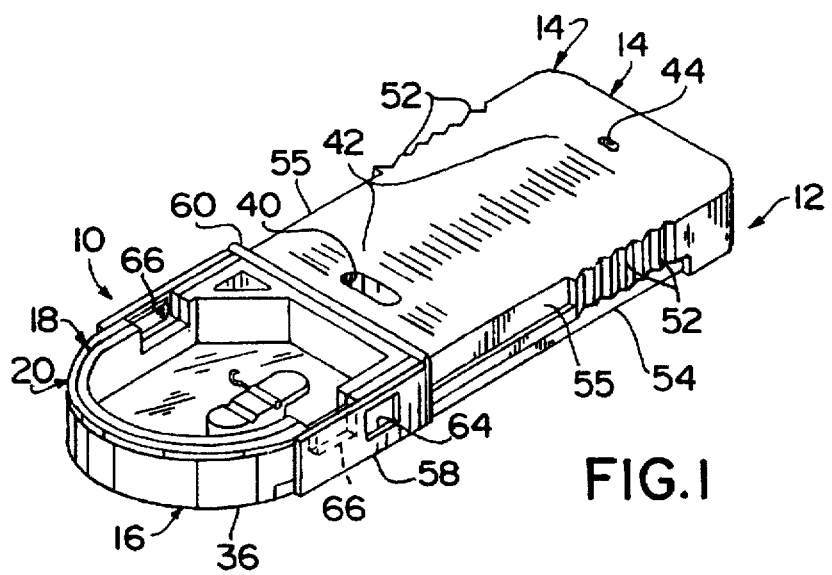
FIG. 1 is a perspective view of a package according to the present invention in an assembled condition.
Figure 2:
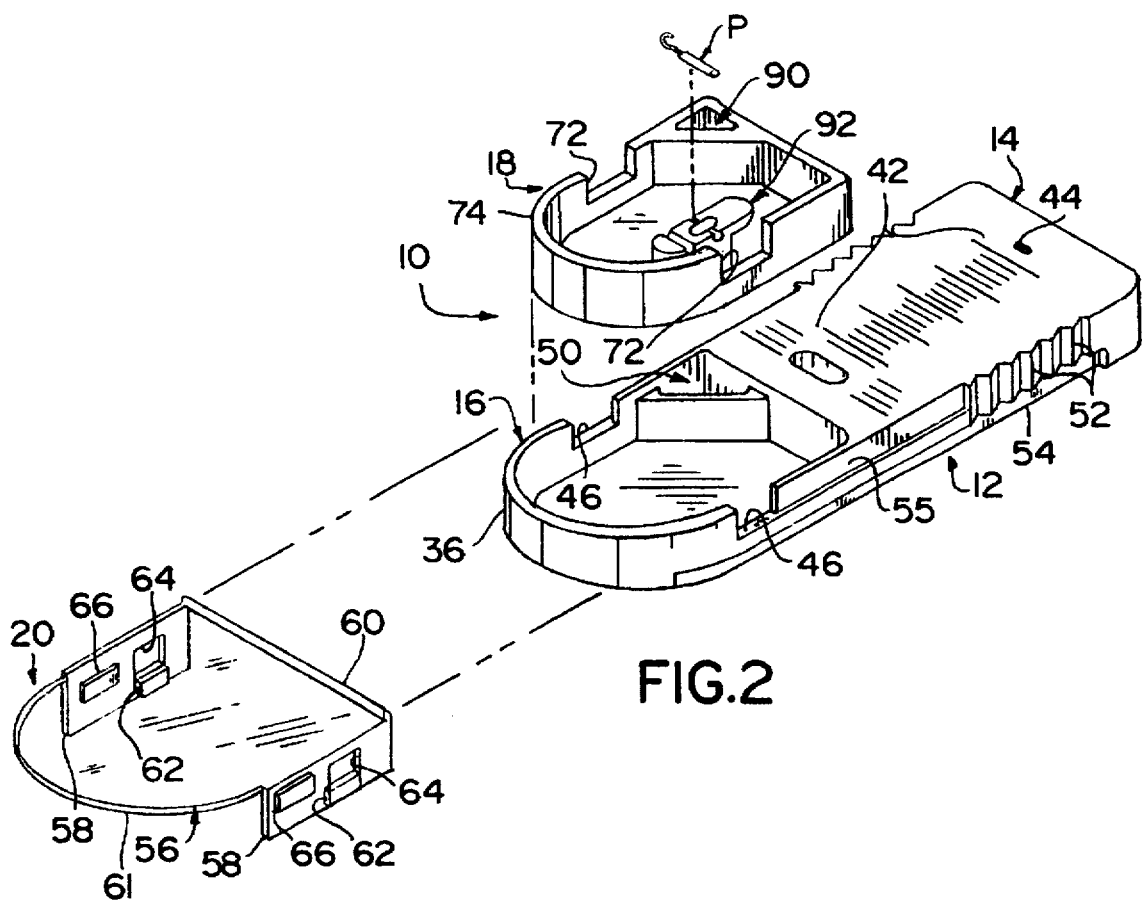
FIG. 2 is an exploded perspective view of the package of FIG. 1 showing the tray, the insert and the lid thereof.

A package 10 according to the present invention, as illustrated in FIGS. 1 and 2, includes a tray 12 with an elongate handle 14 and a compartment 16 disposed at the distal end of the handle, an insert 18 removably disposed within the compartment for holding a medical implant, such as a wire piston prosthesis, in a specific orientation relative to the tray, and a lid 20 mounted on the tray for sliding movement between an extended or closed position where the lid is disposed over the compartment to cover the insert and a retracted or open position where the lid is proximally spaced from the compartment to expose the insert. Tray 12 can be formed in any suitable manner using appropriate medical grade materials but is preferably formed of a relatively rigid plastic material, that is, a plastic material such as, for example, polypropylene, styrene or acrylic, having a Shore A durometer equal to or greater than about 90. In a preferred embodiment, the tray is injection molded as an integral one-piece unit with an opaque coloring to provide better contrast with the medical implant, e.g., a wire piston prosthesis, thereby permitting improved visualization of the implant. Handle 14 is substantially solid and, as best seen in FIGS. 3 and 4, the handle includes generally rectangular top and bottom surfaces 22 and 23, front and rear surfaces 24 and 26 transversely connecting respective front and rear edges of the top and bottom surfaces, and side surfaces 28 and 30 transversely connecting opposed lateral edges of the top and bottom surfaces. Compartment 16 is disposed at the distal end of the handle and includes a pair of laterally opposed side walls 32 and 34 extending in parallel from laterally opposed edges of the front surface of the handle in a distal direction and a forward wall 36 of arcuate or curved configuration forming a curved connection between the side walls. A bottom wall 38 of the compartment extends from the bottom edge of the front surface of the handle between respective bottom edges of side walls 32 and 34 and forward wall 36 to form a closed bottom for the compartment.

Top surface 22 of the handle is generally planar and is preferably configured for use as a trimming board. To this end, the top surface is provided with a recess or hole 40 of oblong configuration near the front edge of the handle and scale markings 42 proximally spaced from the recess at regular longitudinal intervals. This permits middle ear prostheses having platforms or enlarged heads at a proximal end, such as so-called "Totals" and "Partials", to be laid upon the surface of the handle with their heads in the recess and their shafts extending therefrom along the markings to be measured and trimmed to length. A small footplate recess or hole 44 can also be formed in the top surface adjacent the rear edge of the handle to hold a stapes footplate shoe to make it easier to assemble the prosthesis with the shoe once the prosthesis is trimmed to length.

Compartment 16 is defined by the bottom wall 38, the front surface 24 of the handle, side walls 32 and 34 and forward wall 36, with the front handle surface, side walls and forward wall extending vertically upward from the bottom wall to define an open top for the compartment when the package is held in a horizontal position as shown in FIG. 2. A pair of recesses or cut-outs 46 of generally rectangular configuration are formed in laterally opposed relation along respective upper edges of the side walls of the compartment and are of sufficient width and depth to provide clearance for the jaws of a forceps. A partition wall 48 extends diagonally relative to a longitudinal axis of the tray between the front surface 24 of the handle and side wall 32 of the compartment to define a subcompartment 50 of generally triangular configuration within compartment 16.

Laterally opposed surfaces 28 and 30 of the handle are shown with serrations 52, that is, a series of consecutive V-shaped cuts oriented vertically along a portion of the handle between front and rear surfaces thereof as shown in FIGS. 1–4 to improve the ability of the user to grip the handle. A first pair of slots or grooves 54 are formed in respective laterally opposed walls and surfaces of the tray along bottom edges thereof and extend from open distal ends disposed adjacent the curved forward wall of the compartment to closed proximal ends defining vertical stops or abutments proximally spaced from handle serrations 52. A second pair of slots or grooves 55 formed in respective laterally opposed walls and surfaces of the tray along upper edges thereof extend between recesses 46 in side walls 32 and 34 and the handle serrations.

Lid 20 can be formed of any medical grade material but is preferably formed of a transparent and rigid material, such as acrylic or polycarbonate, that allows the prosthesis to be visualized through the lid when the lid is in the extended or closed position covering the compartment. The lid includes a cover plate 56 having a configuration to cover the compartment and a pair of generally rectangular, plate-like legs 58 extending vertically downward from laterally opposed edges of the cover plate. A proximal edge of the cover plate is provided with an upwardly or outwardly extending ridge or lip 60 to provide a surface against which a force can be applied to the lid. A distal edge 61 of the plate is provided with a curvature corresponding to that of compartment wall 36 and is spaced from proximal edge 60 so that, when the curved distal edge of the plate is longitudinally aligned with the curved wall of the compartment, the proximal edge of the plate will be disposed proximally of or adjacent the front surface of the handle to provide complete coverage of the compartment. As best seen in FIGS. 5 and 6, legs 58 of the lid include inwardly protruding pads 62 of rectangular configuration oriented to slide within slots 54 along bottom edges of the tray when the lid is assembled with the tray as shown in FIG. 1. A rectangular opening 64 is formed above each pad by the molding tools, and a second set of rectangular pads 66 are disposed at about the same elevation as openings 64 but are distally spaced therefrom to protrude into recesses 46 in the side walls of the tray when the lid is in the closed position shown in FIG. 1.

Insert 18 is configured to fit snugly within compartment 16 and, as best seen in FIGS. 7 and 8, the insert includes a pair of laterally opposed side walls 68 and 70 of unequal length with generally rectangular recesses 72 formed therein in opposed relation, a forward wall 74 of arcuate configuration forming a curved connection between the side walls, a rear wall 76 extending perpendicularly from a proximal end of the longer side wall 70 to a diagonal wall 78 joining the rear wall with the proximal end of the shorter side wall 68, and a bottom wall 80, the aforesaid walls cooperating to define a compartment 81 having a configuration to fit conformably within compartment 16 of the tray. A second diagonal wall 82, parallel to the first diagonal wall 78 but proximally spaced therefrom to define a channel therebetween for receiving partition 48 of the tray, is attached to the first diagonal wall with a web 84 and extends between a rear wall 86 and side wall 88 perpendicular to the rear wall to define a subcompartment 90 of generally triangular configuration having a generally triangular bottom wall 91 spaced above bottom wall 80. Subcompartment 90 fits conformably within the triangular subcompartment 50 of the tray to hold medical implants smaller in size than a wire piston prosthesis. A pedestal 92 extends vertically upward from bottom wall 80 of the insert to hold a wire piston prosthesis P in a specific orientation or position relative to the recesses formed in the side walls of the compartment and the insert. The pedestal is laterally offset from the longitudinal axis of the insert to provide space for instruments and fingers to be inserted between the pedestal and the upwardly extending walls of the compartment; and, as best seen in FIGS. 9 and 10, the pedestal includes a mounting block 94 with a top surface 95 spaced slightly below an upper edge 97 of the walls of the insert. An elongated trough, recess, or slot 98 is formed in the top surface of the block perpendicular to the longitudinal axis of the insert and in longitudinal alignment with recesses 72 formed in side walls 68 and 70. The slot is configured to hold an elongate, cylindrical piston, shaft or rod R at the distal end of the wire piston prosthesis P in a horizontal position above the bottom wall of the insert and respective lower edges 99 of recesses 72, with a longitudinal axis of the rod R being aligned with the recesses and the wire loop W at the proximal end of the rod protruding from the block to permit a forceps introduced through one of the recesses to grasp the wire loop at the proximal end of the prosthesis for proper presentation of the distal end at the operative site. One edge of the piston storage slot is provided with a resilient flap 100 that overlaps or extends over the prosthesis P to assist in holding the prosthesis in place during transport and handling of the package. A lever arm 96 extends rearwardly from block 94 in the manner of a cantilever and pivots about a hinge or fulcrum 101 disposed immediately beneath slot 98 so that downward movement of the lever arm causes the slot to expand or open, thereby releasing the prosthesis held therein. The lever arm is biased toward an elevated position canted slightly downward relative to the top surface of the block, and a rib 102 may optionally be located between the lever and the block to assist in biasing the lever upwardly, looking at FIG. 10, so that a constant pressure is exerted on the prosthesis over time to prevent the prosthesis from coming loose during shipping and handling or under the effects of gravity when stored for long periods of time. A well or cavity 103 of generally oblong configuration is formed in the top surface of the block in transverse relation to slot 98 and is of suitable length, width and depth to provide clearance for jawed instruments, such as tweezers, used to load a prosthesis into the slot during manufacture and assembly. Typically, the rod or shaft of the prosthesis is held between jaws of the loading instrument in perpendicular relation thereto such that tips of the jaws are disposed in the cavity as the prosthesis is placed in the slot. This allows easier and more precise positioning of the prosthesis in the slot. One or more additional recesses, slots or troughs can be formed in other parts of the pedestal as shown, for example, in FIG. 10 at 104, to hold medical implants of larger size and/or which do not require a specific orientation for proper presentation at an operative site.

The insert can be formed of any suitable medical grade material but is preferably formed of a soft and flexible material, that is, a material having a Shore A durometer of between about 20 and about 90, with about 65 being presently preferred, such as, for example, injection molded thermoplastic elastomers or urethanes, or softer materials such as compression molded Evasote or pressure formed polyethylene foam. Use of a soft and flexible material for the insert reduces the chance for breakage of the prosthesis during shipping, allows the forceps to "dig into" the material and get under the prosthesis for better presentation, permits the lever arm to be easily depressed and forms a seal with the lid when it is closed in order to contain small products in the package.

Package 10 is preferably supplied in the assembled condition, shown in FIG. 1, with insert 18 received within compartment 16 of tray 12 and lid 20 slidably mounted on the tray in a closed position covering the compartment. The base or body of a wire piston prosthesis P is held by pedestal 92 in a horizontal position above the bottom wall of the insert with a longitudinal axis of the piston being aligned with recesses 72 in the side walls of the insert and the wire loop at the proximal end of the piston being positioned in an exposed, easily graspable position in the space between the pedestal and one of the recesses. In the closed position, cover plate 56 of the lid contacts upper edges of the insert to form a seal therewith and legs 58 of the lid extend downwardly from opposite sides of the plate to cover recesses 46 and 72 in the tray and insert, respectively, with pads 66 on the inner surface of the legs protruding into the recesses to lock the lid in the closed position. The assembled package thus forms a capsule containing the wire piston prosthesis, which is held firmly in place within storage slot 98 at the top of pedestal 92 and is prevented from moving during transport, sterilization and delivery to maintain the above-specified orientation.

Figure 11:
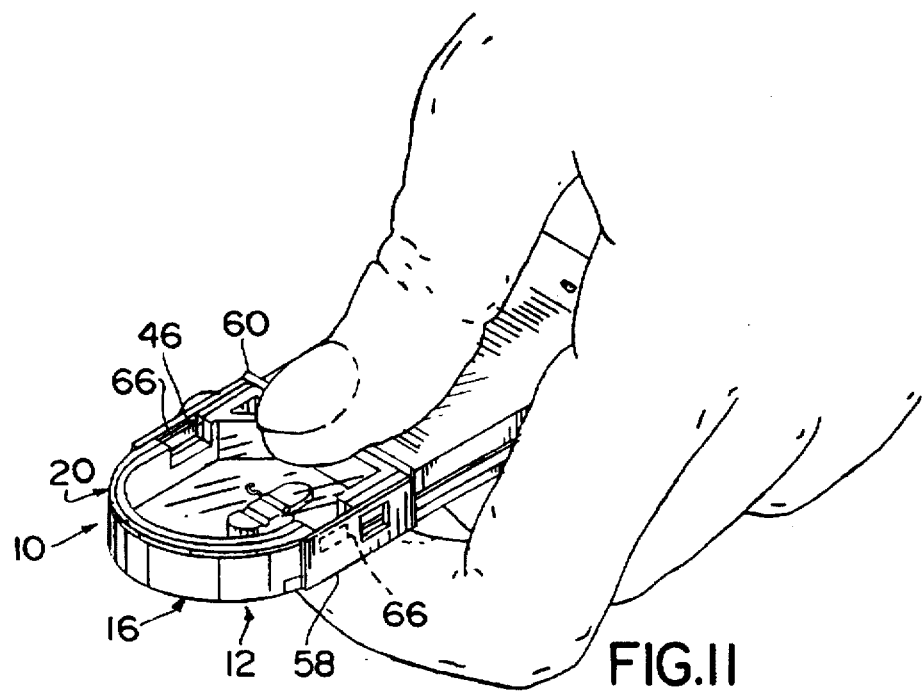
FIGS. 11 and 12 are perspective views illustrating use of the package of the present invention to deliver a wire piston prosthesis.
Figure 12:
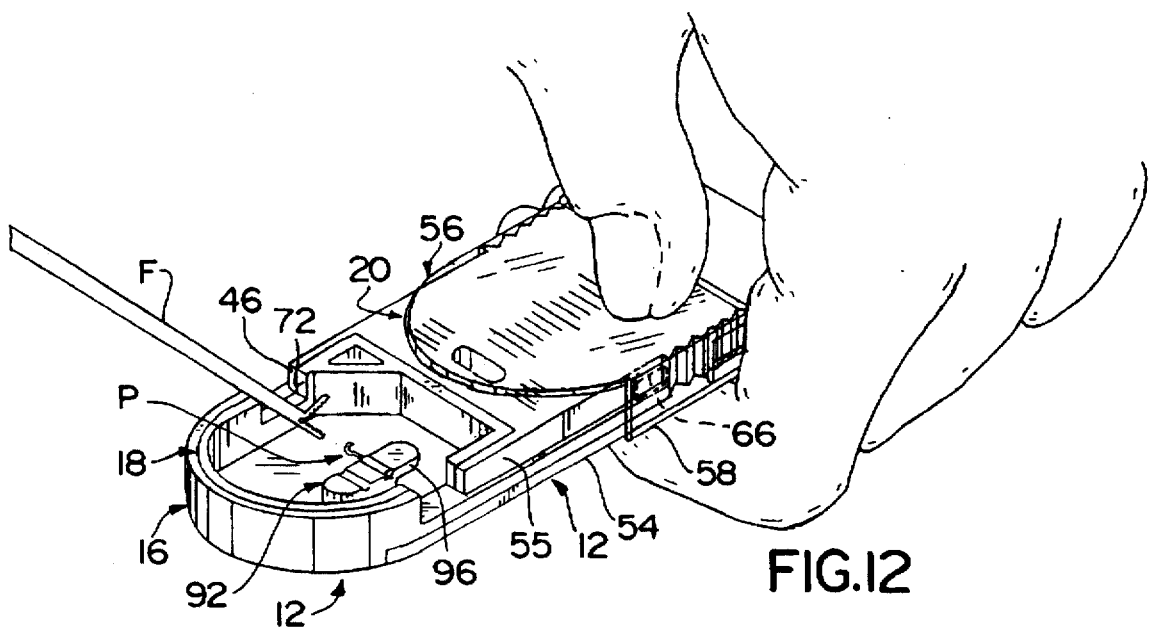

The stapes piston P can be removed from package 10 by holding the package in a horizontal position as shown in FIG. 11, for example with the thumb on lid 20 and one or more fingers of the hand supporting the bottom of tray 12, and sliding the lid 20 proximally relative to the tray to move the lid from the closed position shown in FIG. 11 to the open position shown in FIG. 12. Lip 60 on the rear edge of lid 20 provides a surface against which the thumb can act to apply a rearwardly directed force directly to the lid so that, when a rearwardly directed force of sufficient magnitude is applied, pads 66 on the interior of the lid are caused to move proximally from within recesses 46 formed in the compartment side walls into slots 55 formed on opposite sides of the tray. With lid 20 in the open position, cover plate 56 and legs 58 of the lid are proximally spaced from compartment 16 and recesses 46 and 72, and medical implants disposed within insert 18, such as the wire piston prosthesis P, are exposed and accessible. As mentioned above, the wire piston prosthesis is held by pedestal 92 in a horizontal position above the bottom wall of the insert with a longitudinal axis of the piston aligned with recesses 72 in the side walls of the insert and the wire loop of the piston positioned in an exposed, easily graspable position in the space between the pedestal and one of the recesses. The wire piston prosthesis is removed from the insert by maneuvering a grasping forceps F into the compartment, preferably from the side via recesses 46 and 72, such that a longitudinal axis of the forceps is aligned with, or substantially aligned with, the longitudinal axis of the piston and the jaws of the forceps are disposed in the space between the pedestal and side walls of the insert in a position to grasp the wire loop at the proximal end of the piston. Since recesses 46 and 72 are formed in pairs on opposite sides of the pedestal, it will be appreciated that the forceps can be introduced from either side of the compartment depending upon the orientation of the prosthesis. If the insert is formed of a soft material, the forceps may be pressed against the pedestal material around the wire piston prosthesis, if desired, to cause the material to be deformed in a manner to permit a larger portion or particular feature of the prosthesis to be grasped. With the proximal end of the prosthesis firmly grasped by the forceps, lever arm 96 of the pedestal is pressed downwardly in the direction of the bottom wall of the insert to pivot lip 100 of the storage slot away from the piston. The prosthesis is thus released from the pedestal such that the forceps can be used by the surgeon to remove the prosthesis from the package, for example by sliding the prosthesis out of slot 98 in a longitudinal manner, and to directly position the distal end of the prosthesis into the middle ear without repositioning or reorienting the prosthesis in the jaws of the forceps. Accordingly, grasping of a wire piston prosthesis is facilitated in a manner to expedite implanting of the prosthesis in accordance with the present invention. Moreover, since the wire piston prosthesis is firmly held in a specified orientation within the compartment until it is grasped, there is less risk of the prosthesis falling out of the compartment or being improperly grasped, reducing the risk of contamination.

From the above, it will be appreciated that the package according to the present invention permits a small medical implant, such as a wire piston prosthesis, to be maintained in a specified orientation or position within a tray or compartment to facilitate removal of the implant from the tray or compartment with a forceps for proper presentation at an operative site. Although the package has been shown and described herein as including a tray having a single compartment containing a pedestal for mounting a medical implant in a specified orientation, the tray can have any number of compartments, each containing one or more pedestals, and can also combine compartments containing pedestals with empty compartments of various size and shape. The compartments can have any configuration when viewed from above in plan including, but not limited to, elliptical and polygonal configurations and combinations thereof, and can have any length, width or depth suitable for accommodating and confining a single type of medical implant or various types of medical implants.

The pedestal of the present invention can take the form of a support mounted on a wall of the compartment and/or spaced from one or more walls of the compartment to accommodate jaws of a forceps and/or a finger therebetween. When the pedestal is provided with a storage slot to hold medical implants, the slot can be oriented in a plane parallel to a bottom wall of the compartment or inclined at any angle relative to the bottom wall and can have any azimuthal orientation within such planes.

The pedestal of the present invention can extend upwardly from the bottom wall of an insert disposed within a compartment of the tray, or the pedestal can be mounted directly in the compartment without an insert. When an insert is used to mount the medical implant within the compartment, the insert can be formed with or without walls that extend upwardly from the bottom of the insert when the tray is held or oriented in a horizontal position. In addition, walls of the insert and/or the compartment can be formed without recesses and/or disposed above the elevation of a medical implant held on the pedestal so long as the medical implant is appropriately oriented.

The handle shown at the proximal end of the tray can be solid or hollow and can have any suitable configuration to be held during the medical procedure. For example, the handle can be of elliptical or polygonal configuration in transverse cross-section with planar or non-planar top and bottom surfaces, straight or curved sides, and with or without serrations, ribs or finger grips formed thereon. Furthermore, the handle can be oriented at any angle relative to a longitudinal axis of the compartment or the bottom wall thereof. When scale markings and/or recesses are provided for measuring and trimming a prosthesis on the handle, the markings can be oriented at any angle relative to a longitudinal axis of the handle and can be printed in English or metric units, as desired. For example, the scale markings can be longitudinally spaced at one millimeter intervals with every fifth millimeter line being longer than the intermediate lines as shown in FIG. 3.

The lid can have any configuration to cover the compartment when closed and can be slidably mounted on the tray as shown or mounted in any suitable manner including, but not limited to, being integrally connected to the tray with hinges, being telescopically received in or on the tray, and being detachable from the tray and held in place by detents or other suitable fasteners.

The various components of the package are preferably formed as molded parts using medically-acceptable plastic materials but can be fabricated using other medically-acceptable materials and can be transparent or opaque, provided with openings, cavities or recesses to reduce weight or cost and/or fabricated as separate parts and assembled using adhesives or suitable fasteners.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. In combination, a medical implant and a package for sterile delivery of said medical implant, said package comprising
   a tray defining a compartment having a bottom wall and at least one wall extending upwardly from said bottom wall when said tray is oriented horizontally;
   a lid configured to cover said compartment; and
   means for holding said medical implant in a specified position above said bottom wall of said compartment during transport and removal;
   wherein at least a portion of said at least one wall is lower than said medical implant in said specified position and wherein a longitudinal axis of said medical implant in said specified position is aligned with said lower portion of said at least one wall to permit said medical implant to be grasped with a forceps positioned along said lower portion of said at least one wall and having a longitudinal axis substantially aligned with said longitudinal axis of said medical implant.

2. A combination as recited in claim 1 wherein said means for holding said medical implant above said bottom wall includes a pedestal extending upwardly from said bottom wall when said tray is oriented horizontally and having a storage slot formed therein to orient said medical implant towards said lower portion of said at least one wall of said compartment.

3. A combination as recited in claim 2 and further comprising an insert removably disposed within said compartment and including a bottom wall, wherein said pedestal extends upwardly from said bottom wall of said insert to hold said medical implant in said specified position.

4. A combination as recited in claim 3 wherein said insert further includes at least one wall extending upwardly from said bottom wall when said insert is oriented horizontally and wherein at least a portion of said upwardly extending insert wall is lower than said medical implant and aligned with said lower portion of said upwardly extending compartment wall.

5. A combination as recited in claim 3 wherein said tray is formed of a relatively rigid material having a Shore A durometer greater than about 90 and said insert is formed of a relatively soft material having a Shore A durometer of between about 20 and about 90.

6. A combination as recited in claim 1 wherein said lower portion of said upwardly extending wall is part of a recess formed in said wall in alignment with said longitudinal axis of said medical implant.

7. A combination as recited in claim 6 and further comprising a plurality of upwardly extending walls and a plurality of recesses formed therein in opposed relation along said longitudinal axis of said medical implant.

8. A combination as recited in claim 1 wherein said tray further includes a handle disposed proximally of said compartment.

9. A combination as recited in claim 8 wherein said medical implant is a middle ear prosthesis and said handle includes a planar surface with scale markings for measuring and trimming said middle ear prosthesis.

10. A combination as recited in claim 9 wherein said handle further includes a recess formed in said planar surface adjacent said scale markings for receiving an enlarged head of said middle ear prosthesis to stabilize said prosthesis as it is being measured and trimmed.

11. A combination as recited in claim 10 wherein said handle further includes a recess formed in said planar surface adjacent said scale markings for holding a stapes footplate shoe.

12. A combination as recited in claim 1 wherein said lid is slidably mounted on said tray and movable between an extended, closed position covering said compartment and a retracted, open position exposing said compartment.

13. A combination as recited in claim 12 wherein said lid includes means for engaging said lower portion of said upwardly extending wall to lock said lid in said closed position.

14. In combination, a medical implant and a package for sterile delivery of said medical implant, said package comprising a tray defining a compartment having a bottom wall;

a lid configured to cover said compartment; and a pedestal extending upwardly from said bottom wall of said compartment when said tray is oriented horizontally, said pedestal including a slot configured to hold said medical implant in a specified position above said bottom wall of said compartment and a lever arm extending in cantilevered relation to said slot and movable between an elevated position holding said medical implant in said slot and a depressed position releasing said medical implant from said slot.

15. A combination as recited in claim 14 wherein said compartment further includes at least one wall extending upwardly from said bottom wall when said tray is oriented horizontally, at least a portion of said upwardly extending wall being lower than said medical implant in said specified position, and wherein a longitudinal axis of said medical implant in said specified position is aligned with said lower portion of said upwardly extending wall to permit said medical implant to be grasped with a forceps positioned along said lower portion of said upwardly extending wall and having a longitudinal axis substantially aligned with said longitudinal axis of said medical implant.

16. A combination as recited in claim 14 wherein said pedestal further includes an elongate cavity formed therein in transverse relation to said slot to provide clearance for jawed instruments used to load said medical implant into said slot during manufacture and assembly.

* * * * *